(12) United States Patent
Cabaret et al.

(10) Patent No.: US 11,547,650 B2
(45) Date of Patent: Jan. 10, 2023

(54) HIGHLY MINERAL-FILLED ADHESIVE BANDAGE OR PATCH

(71) Applicant: SILAB S.A, Objat (FR)

(72) Inventors: Cyrille Cabaret, Segur le Chateau (FR); Camille Benetollo, Brive (FR); Elodie Georges, Brive (FR); Agnès Jeanne Marie-Louise Claus, Limoges (FR); Vincent Maurice Gloaguen, Aixe sur Vienne (FR)

(73) Assignee: Silab S.A, Objat (FR)

( * ) Notice: Subject to any disclaimer, the term of this patent is extended or adjusted under 35 U.S.C. 154(b) by 0 days.

(21) Appl. No.: 15/528,962

(22) PCT Filed: Nov. 12, 2015

(86) PCT No.: PCT/EP2015/076419
§ 371 (c)(1),
(2) Date: May 23, 2017

(87) PCT Pub. No.: WO2016/083141
PCT Pub. Date: Jun. 2, 2016

(65) Prior Publication Data
US 2017/0258698 A1    Sep. 14, 2017

(30) Foreign Application Priority Data

Nov. 27, 2014 (FR) ...................... 1461592

(51) Int. Cl.
| | | |
|---|---|---|
| *A61K 8/73* | (2006.01) | |
| *A61Q 19/00* | (2006.01) | |
| *A61K 8/02* | (2006.01) | |
| *A61K 8/25* | (2006.01) | |
| *A61K 8/26* | (2006.01) | |
| *A61K 8/34* | (2006.01) | |
| *A61K 8/49* | (2006.01) | |
| *A61K 8/98* | (2006.01) | |
| *B29C 41/00* | (2006.01) | |
| *B29C 41/02* | (2006.01) | |
| *B29C 41/46* | (2006.01) | |
| *B29K 105/16* | (2006.01) | |
| *B29L 7/00* | (2006.01) | |
| *B29L 31/00* | (2006.01) | |

(52) U.S. Cl.
CPC .............. *A61K 8/73* (2013.01); *A61K 8/0208* (2013.01); *A61K 8/25* (2013.01); *A61K 8/26* (2013.01); *A61K 8/345* (2013.01); *A61K 8/4973* (2013.01); *A61K 8/98* (2013.01); *A61Q 19/00* (2013.01); *B29C 41/003* (2013.01); *B29C 41/02* (2013.01); *B29C 41/46* (2013.01); *A61K 2800/412* (2013.01); *B29K 2005/00* (2013.01); *B29K 2105/16* (2013.01); *B29L 2007/008* (2013.01); *B29L 2031/753* (2013.01)

(58) Field of Classification Search
CPC ... A61K 8/73; A61K 8/98; A61K 8/26; A61K 8/345; A61K 8/4973; A61K 8/25; A61K 8/0208; A61K 2800/412; B29C 41/003; B29C 41/46; B29C 41/02; A61Q 19/00; B29L 2031/753; B29L 2007/008; B29K 2005/00; B29K 2105/16
See application file for complete search history.

(56) References Cited

U.S. PATENT DOCUMENTS

| | | | |
|---|---|---|---|
| 5,735,812 A | 4/1998 | Hardy | |
| 7,491,406 B2 | 2/2009 | Leung et al. | |
| 8,741,266 B2 * | 6/2014 | Boyd | A61K 8/0208 424/49 |
| 2002/0131990 A1 * | 9/2002 | Barkalow | A61K 9/0056 424/439 |
| 2006/0034905 A1 * | 2/2006 | Singh | A61K 9/006 424/449 |
| 2016/0317422 A1 * | 11/2016 | Szewczyk | A61K 8/731 |

FOREIGN PATENT DOCUMENTS

| | | |
|---|---|---|
| EP | 0 613 692 | 7/1994 |
| EP | 0 750 905 | 2/1997 |
| WO | 2014/027873 | 2/2014 |

OTHER PUBLICATIONS

PCT Search Report for PCT/EP2015/076419 (dated Dec. 14, 2015).

* cited by examiner

*Primary Examiner* — Snigdha Maewall
(74) *Attorney, Agent, or Firm* — Greer, Burns & Crain, Ltd.

(57) ABSTRACT

The present invention relates to an adhesive and soluble adhesive bandage or patch comprising a soluble film of natural origin with high mineral content. The soluble film comprises from 20 to 90 wt % of mineral filler and wherein the mineral filler content level is higher than the polysaccharide content level. It also relates to these bandages or patches for use in cosmetics or therapy. Also, a method of making a soluble film.

18 Claims, No Drawings

HIGHLY MINERAL-FILLED ADHESIVE BANDAGE OR PATCH

RELATED APPLICATIONS

This application is a national phase of International Application No. PCT/EP2015/076419 filed on Nov. 12, 2015, which claims priority to French Application No. 1 461 592 filed on Nov. 27, 2014, the entirety of both of which are incorporated herein by reference.

FIELD OF THE INVENTION

The present invention relates to an adhesive and soluble adhesive bandage or patch comprising a soluble film of natural origin with high mineral content. It also relates to these bandages or patches for use in cosmetics or therapy.

BACKGROUND OF THE INVENTION

Soluble bandages are known in the form of water-soluble polymer-based sheets, for example for hydration and skincare, in particular to contribute active ingredients on the skin at the application point of the bandage, such as essential oils or plant extracts (EP 750,905, EP 613,692). Such soluble films can also be used as "mouthwash" by dissolving to release active ingredients once they are placed in the mouth (U.S. Pat. No. 7,491,406).

The incorporation of mineral fillers into polymer compositions of natural origin has been subject to many scientific studies on the physicochemical properties of such mixtures. Sanchez Garcia et al. describes the barrier properties of carrageenan-based compositions, to which different fillers are added, including clay and zein (J. Agric. Food Chem. 2010, 58, 6884-6894). Tunc & Duman describe the preparation and characteristics of nanocomposite films based on methylcellulose and montmorillonite (Applied Clay Science, 5010, 48, 414-424). Wilhelm et al. describes the study of the physicochemical properties of starch-based films, reinforced with clay (Carbohydrate Polymers, 2003, 52, 101-110). Carvalho et al. describes the analysis of thermoplastic compositions based on starch and kaolin (Carbohydrate Polymers, 2001, 45, 189-194). Savanan et al. describes the improved thermal stability of compositions based on chitin and bentonite via a cross-linking agent (Elixir Appl. Chem., 2012, 44, 7374-7377).

However, none of these documents describe films able to be used as an adhesive bandage or patch, in cosmetics or therapy.

It will additionally be noted that what is identified as a "film" in these publications is generally a rigid and breakable product, much more comparable to chips, not corresponding to a film able to be used as an adhesive bandage or patch, in cosmetics or therapy. This is in particular the case for the product described by Tunc & Duman.

It is also known that in such bandages or patches, films based on natural polysaccharides do not comprise high mineral filler content levels, at the very most 15% (WO2006/027873).

However, it remains necessary to improve these soluble films both in terms of their mechanical strength and their stability over time, or to provide a new solution that allows greater versatility in the nature and quantity of active ingredients that can be incorporated into the bandage or patch.

For manufacturing, the use of mineral fillers simultaneously makes it possible to play a surfactant role during the film casting operation, reduce the drying time of the film, and stiffen the film.

During the use of the bandage or patch, and based on the polymer used, the presence of a high filler level makes it possible to reduce the sensitivity of the film to hygrometry and accelerate the drying time on the skin.

BRIEF DESCRIPTION OF THE INVENTION

The invention relates to a bandage or patch comprising a soluble film comprising a natural polysaccharide and mineral filler, characterized in that it comprises from 20 to 90 wt % of mineral filler. The invention more particularly relates to a bandage or patch, characterized in that it comprises from 20 to 90 wt % of mineral filler and in that the mineral filler content level is higher than the polysaccharide content level.

The polysaccharide of natural origin (also called "natural polysaccharide") is advantageously chosen from among polysaccharides, and in particular plant, algae or animal extracts, in particular marine animals such as cellulose derivatives, starch derivatives, chitin derivatives, phycocolloids (such as alginates, carrageenans, agars), vegetable proteins, pectins, gellan, pullulan, gum arabic, especially carrageenans.

The mineral filler is advantageously selected from phyllosilicates, such as kaolin, talc, sodium or calcium montmorillonite, in particular kaolin, or other inorganic forms such as mica, illite, perlite, diatomite or calcium carbonates.

The invention also relates to a bandage or patch comprising a soluble film comprising a polysaccharide and a mineral filler, as substrate for active compounds for their release where the bandage or patch is applied.

The active ingredients are of the water-soluble or liposoluble type, advantageously chosen from among essential oils, phenols, peptides, proteins, amino acids, vitamins, carbohydrates, aromatic spice or plant extracts, etc.

The content level of active ingredients in the soluble film according to the invention is advantageously comprised between 1 and 80%.

The bandage or patch according to the invention has a specific geometric shape, such as parallelepiped, oval, ovoid, etc. It may take the form of a parallelepiped strip that will be cut at the time of use. The bandage or patch according to the invention may be made up solely of the soluble film according to the invention, or may comprise the combination of the soluble film with a substrate, such as an impermeable layer associated with the back of the face of the film intended to adhere to the skin or mucosa.

It in particular differs from a simple film by the fact that it is distributed in a package appropriate for its use in cosmetics or therapy.

The invention also relates to the use of the bandage or patch according to the invention in cosmetics, and the bandage or patch according to the invention for use in therapy.

DETAILED DESCRIPTION OF THE INVENTION

The invention relates to a soluble film comprising a natural polysaccharide and a mineral filler, characterized in that it comprises from 20 to 90 wt % of mineral filler and in that the mineral filler content level is higher than the polysaccharide content level.

Unless otherwise indicated, the percentages are given by weight relative to the total weight of the dry mass of the composition of the film. The dry mass may be obtained by drying the film until complete evaporation of the residual water under conditions that do not deteriorate the components of the film. It may also be calculated by adding the weight of all of the components of the film, with the exception of the water.

A film refers to a sheet having a specific thickness from 20 to 750 µm, preferably from 30 to 200 µm, more preferably from 60 to 120 µm, for example from 60 to 90 µm.

The natural polysaccharide is advantageously chosen from polysaccharides and particularly plant, algae or animal extracts, in particular marine animals such as cellulose derivatives (such as carboxymethyl cellulose, ethyl cellulose, methyl cellulose, ethylmethyl cellulose, ethyl-hydroxyethyl cellulose, hydroxypropylmethyl cellulose, microcrystalline cellulose, cellulose gum), starch and derivatives thereof (modified starches, dextrins, carboxymethyl starch), derivatives of chitin (chitosan), phycocolloids (such as alginates, carrageenans, agars), pectins, pullulan, gums (gum arabic, gellan, xanthan, locust bean, guar, tara, karaya, ghatti, tragacanth, cassia), waxes (beeswax, candelilla, carnauba, sugar cane), in particular carrageenans.

In light of their high molecular weight (e.g., 150,000 to 500,000 Da) and the length of the monomer chains, the aforementioned natural polymers have good natural film-forming properties. The film-forming properties also depend on the presence of hydrogen functions (in particular of type OH or COOH) that favor the interactions between molecules, and therefore film formation. Among polysaccharides, several families of polymers meet this definition and will be favored to form films, such as cellulose derivatives, starch derivatives, chitin derivatives (chitosan), pectins or algae derivatives (alginates, carrageenans).

The mineral filler is advantageously selected from phyllosilicates, such as kaolin, talc, sodium or calcium montmorillonite, attapulgite, in particular kaolin, or other inorganic forms such as mica, illite, perlite, vermiculite, halloysite, diatomite, carbonates or bicarbonates (calcium, sodium, potassium, magnesium, ammonium), marble.

The mineral fillers used in bandages or patches have a mean particle size generally ranging from 1 to 15 µm. A possible pretreatment by an emulsifier of the rotor-stator type, by microwave, by micro-grinding (High Energy Ball Milling type), by ultrasound or suspension in water, makes it possible to obtain exfoliation of the mineral filler and to lower the size of the clusters.

According to one particular embodiment of the invention, the film also comprises a surfactant agent typically used in cosmetic or pharmaceutical compositions, in particular chosen from among non-ionic, anionic or cationic surfactants, preferably from among non-ionic surfactant agents. These in particular include lecithins, sorbitan and fatty acid esters, and derivatives thereof, in particular those marketed under the names Span and Tween (polysorbate), in particular sorbitan monolaurate (Span 20), or sorbitan mono stearate. One skilled in the art will know how to identify the appropriate surfactant agents based on the intended use of the product according to the invention.

According to one particular embodiment of the invention, the film also comprises a plasticizer agent typically used in cosmetic or therapeutic compositions. These in particular include glycerol, polyethylene glycol and sorbitol.

The invention also relates to a bandage or patch comprising a soluble film comprising a polysaccharide and a mineral filler, as substrate for active compounds for their release where the film will be applied in bandage or patch form. Based on its formulation, the film may act as an active substrate by beneficially influencing the release of the active ingredients on and in the skin, in an accelerated or delayed manner, or by facilitating the transcutaneous penetration of the active ingredients.

According to the invention, "active ingredient" refers to any mineral or organic compound that exercises a biological action on or through the skin of the individual on which it is applied. This biological activity can be an antiseptic, antifungal or antibiotic action, a hydrating action, a firming action, an occlusive action, a cleansing action, an action intended to favor local muscle heating, a local antalgic action, a hemostatic action, a repellent and/or insecticidal action, or any other dermatological action.

The active ingredients are water-soluble or liposoluble, advantageously chosen from among essential oils, vegetable oils, phenols, peptides, extracts of spices or plants, plant amino acids and proteins, vitamins, carbohydrates, urea, acids (hyaluronic acid), mixtures thereof, derivatives thereof or any other ingredient or active ingredient of interest in dermo-cosmetics or therapeutic applications, etc.

Among natural active ingredients, examples include essential oils recognized for their natural antiseptic, antifungal, antibacterial or cicatrizing activity, polyphenols recognized for their antioxidant activity.

It is understood that compounds used for their plasticizing properties, such as glycerin, are not among the active ingredients within the meaning of the present invention.

The film according to the invention may comprise any other additives typically used in cosmetic or pharmaceutical formulations, such as dyes, flavors, scents, etc.

The content level of the components of the film according to the invention will depend, and be adapted by one skilled in the art based, on the nature of the components used and the desired physicochemical properties of the film, such as its physical properties to withstand storage and transport, its ability to adhere to the skin depending on its degree of moisture, its disintegration speed in water, or its ability to control the release of the incorporated active ingredients and/or by improving transcutaneous penetration.

In particular, to produce a bandage or patch according to the invention, one seeks for the plasticity of the film to allow use in the form of a flexible film. The material must not break and must withstand sufficient deformation for application in patch form. These properties are in particular characterized by a measurement of the Young's Modulus, the values of which will generally be comprised between 500 and 2,000 MPa (at 25° C.–stretching speed 2 mm/min), and a Rupture Stress generally comprised between 15 and 30 MPa.

The measurement of the Young's Modulus and the Rupture Stress is done according to the standard methods well known by those skilled in the art. One specific example of this is the uniaxial pulling/stretching method, by using dumbbell-type specimen with an effective length of 22 mm, a width of 6 mm, and a thickness of about 200 µm on a tensile testing machine of the Instron® 4466 type.

The mineral filler content level is comprised between 20 and 90 wt %, advantageously at least 25%, in particular between 30 and 80%, at least 50% for one advantageous embodiment of the invention. The filler content level will depend on the presence or absence of active ingredient, and in particular the hydrophilic or lipophilic nature of the active ingredient.

In the presence of active ingredients, the filler content level may be less than 50% depending on the quantity of active ingredients comprised in the final composition.

The polysaccharide content level is advantageously chosen from 5 to 49 wt %, preferably from 5 to 35 wt %, advantageously from 5 to 25 wt %, advantageously from 10 to 20 wt %.

According to one particular embodiment of the invention, the mineral filler/natural polysaccharide weight ratio is greater than 1, preferably at least 1.5, in particular at least 1.8, more preferably at least 2, according to the desired uses and properties for the bandage or patch according to the invention. According to the properties of the film desired by one skilled in the art, this weight ratio may reach up to 6. For certain embodiments, this weight ratio is comprised between 1.8 and 2.5, advantageously about 2. For other embodiments, this weight ratio is comprised between 3.5 and 4.5, about 4.

The content level of active ingredients in the soluble film according to the invention is advantageously comprised between 1 and 80%, in particular between 1 and 50%.

The content level of surfactant agent, when present in the composition, is advantageously from 0.2% to 5%.

The content level of plasticizing agent, when present in the composition, may reach up to 40%. More generally, it will be comprised between 5 and 30%, advantageously from 10% to 20%. One skilled in the art will know how to choose the plasticizer content level based on the physicochemical properties of the film of the patch or bandage according to the invention.

Advantageously, the film comprises a plasticizer, the plasticizer/total filler and polysaccharide weight ratio ranging from 0.2 to 0.3. Preferably, this plasticizer/(mineral filler+polysaccharide) weight ratio is about 0.25. The invention in particular relates to the preferred compositions according to the invention, with or without active ingredients.

Composition without Active Ingredient:

| | |
|---|---|
| Mineral filler | 50 to 70% |
| Natural polymer | 10 to 30% |
| Surfactant | 0 to 2% |
| Plasticizer | 0 to 30% |

Composition with Water-Soluble Active Ingredient:

| | |
|---|---|
| Mineral filler | 40 to 60% |
| Natural polymer | 10 to 25% |
| Surfactant | 0 to 2% |
| Plasticizer | 0 to 30% |
| Water-soluble active ingredient | 1 to 25% |

Composition with Liposoluble Active Ingredient:

| | |
|---|---|
| Mineral filler | 25 to 50% |
| Natural polymer | 5 to 25% |
| Surfactant | 0 to 2% |
| Plasticizer | 0 to 30% |
| Liposoluble active ingredient | 1 to 45% |

In the foregoing preferred compositions, the mineral filler/polysaccharide weight ratio is greater than 1, as discussed above, and the plasticizer/(mineral filler+polysaccharide) weight ratio ranges from 0.2 to 0.3, as discussed above.

The fragmentation time of the films according to the invention in cold water is advantageously from 10" to 1'; complete solubilization is from 30" to several minutes.

The films according to the invention retain good mechanical strength, in particular necessary for handling, and great flexibility for use as bandages or patches. They are not sticky or oily, and assume a dry galenic form.

The invention also relates to a method for manufacturing a film according to the invention. One skilled in the art knows different methods for manufacturing such films. Preferably, the film is prepared using the "film casting" technique, the principle of which consists of preparing the mixture in liquid form, depositing it on a non-sticky substrate, and evaporating the water by passing it through a drying system, optionally including infrared, oven and ventilation. One skilled in the art will know how to adapt the operating conditions to manufacture the composition of the adopted solution and the drying device that it uses.

In particular, and based on the formulation, the drying parameters will be optimized to allow the formation of a homogenous film, with no bubbles or holes. The drying time may reach up to 20' or more, preferably from 3' to 8', the temperature goes from 50 to 140° C., preferably from 70 to 110° C., for example 80° C.

In the drying device (for example an oven), the ventilation may be adjusted up to 2500 rpm, preferably from 1000 to 1800 rpm, and when infrared is used, an intensity will be chosen preferably reaching up to 25%.

After drying, the soluble film according to the invention has the residual moisture that may reach up to about 10%.

Prior to the formation and drying of the film, work to homogenize the film-forming solution will be done. In particular, in the case of lipidic active ingredients or components, a micro-emulsion operation will be done using an emulsifier or a mixer of the rotor-stator type.

The invention relates to a bandage or patch comprising a soluble film according to the invention or obtained using the method according to the invention. The bandage or patch according to the invention has a specific geometric shape, such as parallelepiped, oval, ovoid, etc. The shape of the bandage or patch will in particular depend on the manner in which it is intended to be applied, and the zone where it is intended to be applied. It may take the form of a parallelepiped strip that will be cut at the time of use. It may have a precut parallelepiped shape for application on flat or tubular areas of the human or animal body (for example limbs, abdomen, back). It may assume an ovoid or bean shape to be applied on moving parts of the human body (for example joints, below the eyelids, etc.). It may assume more complex shapes, such as the shape of a face with cutouts for the eyes and mouth, for application on the face.

The bandage or patch according to the invention may be made up solely of the soluble film according to the invention, or may comprise the combination of the soluble film with a substrate, such as an impermeable or anti-adhesive layer associated with the back of the face of the film intended to adhere to the skin or mucosa, to facilitate the application or handling of the film.

It in particular differs from a simple film by the fact that it is distributed in a package appropriate for its use in cosmetics or therapy.

Such packaging in particular comprises the placement in individual bags made from plastic, aluminum or complex materials, in the form of a distributor/dispenser or in a box.

The invention also relates to the use of the film according to the invention in cosmetics, and the film according to the invention for use in therapy.

Without active ingredients, it can be used for its soothing, occlusive and tightening properties, alone or in combination with solutions or creams. It then makes it possible to act as physical protection and a barrier film.

With an active ingredient, it can be used to extend the contact time between the skin and the active ingredient to improve the efficacy, for example by facilitating transcutaneous penetration.

The bandages or patches are used easily. For an application on an area with dry skin, one need only to slightly moisten the skin before applying the face of the film intended to come into contact therewith. For an application on an area with wet skin, for example with a wound, one need only to apply the face of the film intended to come into contact therewith, to which it will adhere with no other operation.

After use, the bandage or patch is removed by peeling, or can be eliminated by simple cleaning (rinsing) with water, in which the film is soluble.

The films as defined above, before being put in patch or bandage form, and if applicable before packaging, are also part of the present invention.

EXAMPLES

Example 1: Films

The films with the following compositions are prepared according to the method described above. The F/P (mineral filler/polysaccharide) and Pl/(F+P) (plasticizer/sum of the mineral fillers and polysaccharides) weight ratios are calculated. Their Young's Moduli, their Rupture Stresses and their Deformation are measured using the uniaxial pulling/stretching method, by using dumbbell-type specimen with an effective length of 22 mm, a width of 6 mm, and a thickness of about 200 μm on a tensile testing machine of the Instron® 4466 type.

Film 1: Cosmetic Patch without Active Ingredient

|  | % in the dried Product | % dry mass |
|---|---|---|
| Kaolin | 57.6 | 63.3 |
| Carrageenan | 14.4 | 15.8 |
| Glycerol | 18.0 | 19.8 |
| Span 20 | 1.0 | 1.1 |
| Water | 9.1 | — |
| F/P |  | 4.01 |
| Pl/(F + P) |  | 0.25 |
| Young's Modulus E | In MPa | $200 < E < 500$ |
| Rupture σ | In MPa | $5 < \sigma < 30$ |
| Deformation ε | In % | $5\% < \varepsilon < 10\%$ |

Film 2: Cosmetic Patch with Water-Soluble Active Ingredient

|  | % in the dried Product | % dry mass |
|---|---|---|
| Kaolin | 43.7 | 48.1 |
| Carrageenan | 10.9 | 12.0 |
| Glycerol | 13.7 | 15.0 |
| Span 20 | 0.7 | 0.8 |
| Water-soluble active ingredient | 21.9 | 24.0 |
| Water | 9.1 | — |
| F/P |  | 4.01 |
| Pl/(F + P) |  | 0.25 |
| Young's Modulus E | In MPa | $200 < E < 500$ |
| Rupture σ | In MPa | $5 < \sigma < 30$ |
| Deformation ε | In % | $5\% < \varepsilon < 10\%$ |

Film 3: Cosmetic Patch with Liposoluble Active Ingredient

|  | % in the dried Product | % dry mass |
|---|---|---|
| Kaolin | 32.1 | 35.3 |
| Carrageenan | 8.0 | 8.8 |
| Glycerol | 10.0 | 11.0 |
| Span 20 | 0.5 | 0.6 |
| Liposoluble active ingredient | 40.2 | 44.2 |
| Water | 9.1 | — |
| F/P |  | 4.01 |
| Pl/(F + P) |  | 0.25 |
| Young's Modulus E | In MPa | $200 < E < 500$ |
| Rupture σ | In MPa | $5 < \sigma < 30$ |
| Deformation ε | In % | $5\% < \varepsilon < 10\%$ |

Film 4: Bandage without Active Ingredient

|  | % in the dried Product | % dry mass |
|---|---|---|
| Kaolin | 47.8 | 52.6 |
| Carrageenan | 12.0 | 13.2 |
| HPMC-K | 12.0 | 13.2 |
| Glycerol | 17.9 | 19.7 |
| Span 20 | 1.2 | 1.3 |
| Water | 9.1 | — |
| F/P |  | 2.01 |
| Pl/(F + P) |  | 0.25 |
| Young's Modulus E | In MPa | $200 < E < 500$ |
| Rupture σ | In MPa | $5 < \sigma < 30$ |
| Deformation ε | In % | $5\% < \varepsilon < 10\%$ |

Film 5: Bandage with Water-Soluble Active Ingredient

|  | % in the dried Product | % dry mass |
|---|---|---|
| Kaolin | 41.1 | 45.2 |
| Carrageenan | 10.3 | 11.3 |
| HPMC-K | 10.3 | 11.3 |
| Glycerol | 15.4 | 16.9 |
| Span 20 | 1.0 | 1.1 |
| Water-soluble active ingredient | 12.8 | 14.1 |
| Water | 9.1 | — |
| F/P |  | 2.00 |
| Pl/(F + P) |  | 0.25 |
| Young's Modulus E | In MPa | $200 < E < 500$ |
| Rupture σ | In MPa | $5 < \sigma < 30$ |
| Deformation ε | In % | $5\% < \varepsilon < 10\%$ |

Film 6: Bandage with Liposoluble Active Ingredient

|  | % in the dried product | % dry mass |
|---|---|---|
| Kaolin | 36.0 | 39.6 |
| Carrageenan | 9.0 | 9.9 |

-continued

|  | % in the dried product | % dry mass |
|---|---|---|
| HPMC-K | 9.0 | 9.9 |
| Glycerol | 13.5 | 14.9 |
| Span 20 | 0.9 | 1.0 |
| Liposoluble active ingredient | 22.5 | 24.8 |
| Water | 9.1 | — |
| F/P |  | 4.01 |
| Pl/(F + P) |  | 0.27 |
| Young's Modulus E | In MPa | 200 < E < 500 |
| Rupture σ | In MPa | 5 < σ < 30 |
| Deformation ε | In % | 5% < ε < 10% |

Example 2: Fragmentation and Solubilization Tests

The fragmentation and solubilization in the water times are measured using a method consisting of placing a piece of film (measuring 3 cm×3 cm) in a volume of water (100 ml) at ambient temperature (18 to 25° C.) and with agitation in an Erlenmeyer flask with magnetic laboratory agitator, of type IKA RH basic 2, in median speed position, corresponding to a rotation speed of the magnetic bar of around 500 to 800 revolutions per minute. The fragmentation time corresponds to the period of time after submersion from which the film breaks into pieces of variable size; the solubilization time corresponds to the period of time after submersion from which the film is completely dissolved in the water (no pieces remain visible).

The results are shown in the Table below.

|  | Film 1 | Film 2 | Film 3 | Film 4 | Film 5 | Film 6 |
|---|---|---|---|---|---|---|
| Fragmentation | 11' | 11' | 12' | 8' | 8' | 10' |
| Solubilization | 40' | 40' | 50' | 60' | 60' | 70' |

Example 3: Technical Improvements

The ability to incorporate mineral fillers according to the invention provides one skilled in the art with new technical solutions for producing such films and using them as bandages or patches, in terms of both their physicochemical properties and their capacity to better incorporate lipophilic active ingredients, or in their preparation method.

3.1 Modifications of the mechanical properties: modification of the rigidity of the material. Depending on the nature of the polymer and the mineral filler, it is possible to modify the characteristic mechanics of the film based on the properties desired by one skilled in the art.

For example, it is possible to modify the Young's modulus of a film made up of CMC+20% glycerol from 555 MPa to more than 800 MPa with the addition of 4 g of talc for 1 g of polymer (i.e., an incorporation rate of 400%). Conversely, the addition of 400% kaolin in an alginate-based film+20% glycerol, makes it possible to reduce the Young's modulus from 1100 MPa to 660 MPa.

3.2 Decreased sensitivity to hygrometry: films made from cellulose or hydrocolloid derivatives are generally very sensitive to hygrometry. It has been demonstrated that incorporating a large quantity of mineral filler (filler/polymer ratio>2) made it possible to decrease this sensitivity of the film to hygrometry during conservation under conditions of 25° C.-75% RH. The film with mineral filler is much less sticky than a film with no filler; it is also possible to superimpose layers of film without adhesion to one another, which is not possible for a film with little or no filler.

3.3 Facilitate the incorporation of lipidic/lipophilic active ingredients: the incorporation of a lipid into a polymer solution on an aqueous base requires a particular preparation, and generally results in a release of the lipid during conservation of the film (oily effect). It has been shown that incorporating a large quantity of certain minerals, in particular kaolin (mineral/polymer ratio>2), facilitates the emulsion work and the introduction of a lipidic active ingredient into a film. Furthermore, the affinity of the mineral filler with the lipid makes it possible to limit the release phenomenon, making it possible to produce formulas containing more lipids, without giving the film an oily effect.

3.4 Surfactant role: during the manufacture of a film using a film casting method, it has been shown that incorporating a large quantity of mineral filler (mineral/polymer ratio >2) plays a beneficial surfactant role in limiting the adhesion on the casting substrate (e.g., Teflon substrate) and guaranteeing the homogeneity of the film.

3.5 Improved drying conditions during manufacturing using the film casting technique: it has been shown that it was possible to:

1) lower the drying temperature from 90-95° C. to 70-75° C. (for a drying time of 7 min.) by incorporating 200% kaolin in a carrageenan film at 1%, or 2) decreasing the drying time from 7 min. to 5 min for this same film at a constant temperature of 90° C.

Example 4: Use as Veterinary Bandage

The film can be used as a veterinary bandage or patch. The area to be protected is cleaned and moistened beforehand; the film is applied on the animal's damp skin. If needed, the bandage may also be moistened by spraying or misting with water. When the film is moistened, it adheres to the skin or fur, then dries in about 5-10 min. Once it has dried, the bandage adheres lastingly to the animal's skin or fur.

Depending on the conditions, the bandage may, as desired, either be rinsed off with water, by applying cold or lukewarm water and rubbing gently, in which case the bandage will solubilize and disappear in several tens of seconds; or be left on the skin, in which case, after some time, the bandage will begin to fragment, then gradually, under the combined action of sweating and rubbing, will disintegrate until it has completely disappeared.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

REFERENCES

EP 750,905
EP 613,692

U.S. Pat. No. 7,491,406
US 2006/027873
Sanchez Garcia et al, J. Agric. Food Chem. 2010, 58, 6884-6894
Tunc & Duman, Applied Clay Science, 5010, 48, 414-424
Wilhelm et al., Carbohydrate Polymers, 2003, 52, 101-110
Carvalho et al., Carbohydrate Polymers, 2001, 45, 189-194
Savanan et al., Elixir Appl. Chem., 2012, 44, 7374-7377

The invention claimed is:

1. A bandage or patch comprising:
a soluble film comprising a natural polysaccharide and a mineral filler selected from the group consisting of: phyllosilicates, kaolin, talc, sodium or calcium montmorillonite, attapulgite, mica, illite, perlite, vermiculite, halloysite, diatomite, carbonates or bicarbonates, marble, and mixtures thereof,
wherein the soluble film comprises from 20 to 90 wt % of mineral filler, and
wherein a weight ratio of the mineral filler to the natural polysaccharide is at least 2 and the film is water soluble and dissolves after between 10 seconds to 70 minutes of water exposure.

2. The bandage or patch according to claim 1, wherein the natural polysaccharide is from a plant extract, an algae extract, an animal extract, or a mixture thereof.

3. The bandage or patch according to claim 2, wherein the polysaccharide comprises an extract from a marine animal.

4. The bandage or patch according to claim 2, wherein the natural polysaccharide is selected from the group consisting of: cellulose derivatives, starches and derivatives thereof, chitin derivatives, phycocolloids, pectins, pullulan, gums, waxes, and mixtures thereof.

5. The bandage or patch according to claim 2, wherein the natural polysaccharide comprises a carrageenan.

6. The bandage or patch according to claim 1, wherein the bandage or patch comprises from 5 to 49 wt % polysaccharide.

7. The bandage or patch according to claim wherein the mineral filler comprises kaolin.

8. The bandage or patch according to claim 1, wherein the bandage or patch comprises from 30 to 80 wt % of mineral filler.

9. The bandage or patch according to claim 1, wherein the soluble film further comprises at least one of a surfactant agent and a plasticizing agent.

10. The bandage or patch according to claim 1, wherein the soluble film comprises at least one water-soluble or liposoluble active ingredient selected from the group consisting of essential oils, phenols, peptides, extracts of spices or plants, and mixtures thereof.

11. The bandage or patch according to claim 1, wherein the soluble film comprises from 1 to 50 wt % of active ingredient.

12. The bandage or patch according to claim 1, wherein the weight ratio of the mineral filler to the natural polysaccharide weight ratio is between 2.0 and 2.5.

13. The bandage or patch according to claim 1, wherein the weight ratio of the mineral filler to the natural polysaccharide weight ratio is between 3.5 and 4.5.

14. The bandage or patch according to claim 1, wherein the soluble film comprises a plasticizer and wherein a weight ratio of the plasticizer to the mineral filler and the natural polysaccharide is from 0.2 to 0.3.

15. The bandage or patch according to claim 1, wherein the soluble film comprises:
50 to 70 wt % the mineral filler, 10 to 30 wt % natural polymer, 0 to 2 wt % surfactant, and 0 to 30 wt % plasticizer; or,
40 to 60 wt % the mineral filler, 10 to 25 wt % natural polymer, 0 to 2 wt % surfactant, 0 to 30 wt % plasticizer, and 1 to 25 wt % water-soluble active ingredient; or,
25 to 50 wt % the mineral filler, 5 to 25 wt % natural polymer, 0 to 2 wt % surfactant, 0 to 30 wt % plasticizer, and, 1 to 45% liposoluble active ingredient.

16. The bandage or patch according to claim 1, wherein a thickness of the soluble film is from 20 to 750 μm.

17. A soluble film comprising a natural polysaccharide and a mineral filler selected from the group consisting of phyllosilicates, kaolin, talc, sodium or calcium montmorillonite, attapulgite, mica, illite, perlite, vermiculite, halloysite, diatomite, carbonates or bicarbonates, marble, and mixtures thereof,
wherein the soluble film comprises from 20 to 90 wt % of mineral filler and wherein the mineral filler content level is at least two times greater than the polysaccharide content level, and
and wherein the film is water soluble and dissolves after between 10 seconds to 70 minutes of water exposure.

18. A method for manufacturing the film of claim 17 comprising a natural polysaccharide and a mineral filler selected from the group consisting of: phyllosilicates, kaolin, talc, sodium or calcium montmorillonite, attapulgite, mica, illite, perlite, vermiculite, halloysite, diatomite, carbonates, bicarbonates, marble and mixtures thereof, wherein the soluble film comprises from 20 to 90 wt % of mineral filler and wherein the mineral filler content level is at least two times greater than the polysaccharide content level, wherein the process comprises:
preparing a mixture of components of the film in aqueous liquid form,
depositing the mixture previously obtained on an appropriate substrate, and
evaporating the water by passing through a drying system.

* * * * *